United States Patent [19]
Jones et al.

[11] Patent Number: 6,096,297
[45] Date of Patent: Aug. 1, 2000

[54] UNDERARM COSMETIC COMPOSITIONS WITH LOWER ALKYL ACETATE

[75] Inventors: Francis Jones, Schaumburg; David Allen Brewster, Buffalo Grove, both of Ill.

[73] Assignee: Unilever Home & Personal Care USA, Greenwich, Conn.

[21] Appl. No.: 09/228,369

[22] Filed: Jan. 12, 1999

Related U.S. Application Data

[60] Provisional application No. 60/073,698, Feb. 4, 1998.

[51] Int. Cl.⁷ .............................. A61K 7/32; A61K 7/38; A61K 7/00
[52] U.S. Cl. .............................. 424/65; 424/68; 424/400; 424/401
[58] Field of Search ............................... 424/65, 68, 400, 424/401

[56] References Cited

U.S. PATENT DOCUMENTS

| | | | |
|---|---|---|---|
| 4,243,548 | 1/1981 | Heeb et al. | 252/305 |
| 4,541,951 | 9/1985 | Hall et al. | 510/106 |
| 4,622,221 | 11/1986 | Schlepprick et al. | 424/76.4 |
| 5,441,727 | 8/1995 | Chatterjee et al. | 424/65 |
| 5,700,768 | 12/1997 | Zhong et al. | 510/214 |

FOREIGN PATENT DOCUMENTS

| | | |
|---|---|---|
| 714551 | 9/1954 | United Kingdom . |

*Primary Examiner*—Shelley A. Dodson
*Attorney, Agent, or Firm*—Milton L. Honig

[57] ABSTRACT

An underarm composition is provided which includes $C_1$–$C_6$ alkyl acetate, an underarm active selected from astringent salts and anti-microbial agents, and a carrier. The carrier may include propellant, silicone, ester and liquid paraffin. Methyl and t-butyl acetates are preferred. Acetates allow reduction in the levels of more volatile organics thereby decreasing air pollution. They also reduce formulation greasiness, are less clogging to spray nozzles, cause less metal can corrosion and reduce caking of actives through better resuspension.

9 Claims, No Drawings

UNDERARM COSMETIC COMPOSITIONS WITH LOWER ALKYL ACETATE

This application claims benefit of provisional application No. 60/073,698 Feb. 4, 1998.

BACKGROUND OF THE INVENTION

1. Field of the Invention

The invention concerns underarm cosmetic compositions including lower alkyl acetates as a vehicle for delivery of active components.

2. The Related Art

Alcohols and low molecular weight esters are generally incorporated into antiperspirant or deodorant spray formulations. Ethyl alcohol provides a good suspension medium for active materials such as antiperspirant salts. An improved fragrance lift can also be achieved through the use of alcohol. Unfortunately, high levels of alcohol accelerate detinning, pitting and other forms of corrosion in metal cans. For this reason, commercial products generally are not formulated with alcohol in amounts higher than 10%.

Volatile organic substances such as ethanol are also undesirable for environmental reasons. Government regulations targeting air pollution require the reduction of volatile substances in cosmetic products.

Antiperspirant and deodorant spray formulations also often contain ester emollients such as isopropyl palmitate. These esters are often greasy, stain clothing and in combination with aluminum salts clog spray nozzles. Substitutes are necessary for at least part of the alcohol and ester ingredients normally required for antiperspirant or deodorant spray formulations.

Accordingly, it is an object of the present invention to provide an antiperspirant or deodorant spray composition which can eliminate or minimize ethanol and ester emollient ingredients normally formulated in such compositions.

Another object of the present invention is to provide an antiperspirant or deodorant spray composition with reduced levels of volatile organic compounds.

Still another object of the present invention is to provide an antiperspirant or deodorant spray composition which is less greasy, having a drier skinfeel and less clogging of spray nozzles.

Yet another object of the present invention is to provide an antiperspirant or deodorant spray composition which reduces caking of actives by improving their resuspension within the composition.

A still further object of the present invention is to provide an antiperspirant or deodorant spray composition which minimizes corrosion of its pressurized steel cans.

These and other objects of the present invention will become more apparent from consideration of the following summary and detailed description.

SUMMARY OF THE INVENTION

An underarm composition is provided which includes:

(i) from about 0.1 to about 80% by weight of $C_1$–$C_6$ alkyl acetate;

(ii) an underarm active selected from the group consisting of astringent salts and anti-microbial agents; and (iii) from about 0.1 to about 90% of a pharmaceutically acceptable carrier.

DETAILED DESCRIPTION OF THE INVENTION

Now it has been found that the inclusion of $C_1$–$C_6$ alkyl acetate in antiperspirant or deodorant spray compositions has a number of benefits. These include a less greasy formulation, less clogging of spray nozzles, less metal can corrosion, reduced caking of actives, lower volatile emission through reduction of ethanol content and drier skinfeel.

Suitable alkyl acetates for the present invention are methyl acetate, propyl acetate, isopropyl acetate, butyl acetate, isobutyl acetate, t-butyl acetate, neopentyl acetate, hexyl acetate and combinations thereof. Most preferred are methyl acetate and t-butyl acetate. Methyl acetate is available from the Eastman Chemical Company, Tennessee. Tert-butyl acetate is available from the Arco Chemical Company, Philadelphia, Pa. Amounts of the alkyl acetate may range from about 0.1 to about 80%, preferably from about 1 to about 70%, optimally from about 10 to about 60% by weight.

A second essential component is that of an underarm active which may be an astringent salt or an anti-microbial agent. The astringent salts may be inorganic or organic salts of aluminum, zirconium, zinc and mixtures thereof. Salts useful as astringents or as components of astringent aluminum complexes include aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ$—$XH_2O$ where Q is chlorine, bromine or iodine, where x is 2 to 5 and x+y=6 and x and y do not need to be integers; and where X is about 1 to 6.

Several types of complexes utilizing the above astringent salts are known in the art. For example, U.S. Pat. No. 3,792,068 (Luedders et al.), discloses complexes of aluminum, zirconium and amino acids such as glycine. Complexes reported therein and similar structures are commonly known as ZAG. The ZAG complexes ordinarily have an Al:Zr ratio of from about 1.67 to 12.5 and a Metal:Cl ratio of from about 0.73 to 1.93. The preferred amino acid for preparing such ZAG-type complexes is glycine of the formula $CH_2(NH_2)COOH$. Spherical ZAG, with particle size 1 to 100 microns, is especially preferred.

More specifically, the following is a list of antiperspirant actives which may be useful for the present invention and which have approved listings under the United States Food & Drug Administration, Federal Register. They include aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY.

Amounts of the active astringent salt may range from about 1 to about 40%, preferably from about 5 to about 30%, optimally from about 8 to about 15% by weight of the composition.

Deodorant actives according to the present invention also include materials other than those functioning as antiperspirants. Deodorants should be capable of killing or hindering the growth of microorganisms that generate malodor or that promote the decomposition of body oils into odiferous fatty acids. Most prominent among organic antimicrobial materials are triclosan, triclorban, chlorhexedine and certain fragrant oils known as deo perfumes (e.g. U.S. Pat. No. 4,278,658 to Hooper et al.). Amounts of the organic antimicrobial materials may range from about 0.01 to about 1%, preferably about 0.1 to about 0.5% by weight. Inorganic antimicrobial materials may also serve as deodorant actives. These include zinc oxide, zinc hydroxide, zinc carbonate, zinc phenolsulfonate, magnesium oxide, magnesium hydroxide, magnesium carbonate, lanthanum oxide, lanthanum hydroxide, lanthanum carbonate, sodium bicarbonate and combinations thereof.

A third essential component of the present invention is that of a carrier. Carriers may be selected from propellants, silicones, esters, liquid paraffins and combinations thereof. Amounts of the carrier may range from about 0.1 to about 90%, preferably from about 20 to about 80%, optimally from about 30 to about 70% by weight of the composition.

Propellants typical of compositions according to the present invention are volatile organic compounds of boiling point less than 40° C., preferably less than 20° C. and optimally no higher than 10° C. Suitable propellant classes include $C_1$–$C_6$ hydrocarbons, $C_2$–$C_8$ dialkyl ethers, carbon dioxide and halo hydrocarbons. Among the useful hydrocarbons are propane, isopropane, butane, isobutane, isopentane, pentane and mixtures thereof. Propellants are available under the mark A31 (purely isobutane) and A45 (isobutane/isopropane) from the Phillips Petroleum Company. Most preferred is propellant A50 which is a blend of isobutane/propane. Another useful propellant is dimethyl ether.

Volatile silicones may be incorporated into compositions of the present invention. They can either be cyclic or linear polydimethylsiloxanes. Amounts of this material may range from about 1 to about 80%, preferably from about 15 to about 70% by weight. Commercially they are available from the Dow Corning Corporation as DC 344, 345, 244, 246 and 245.

Non-volatile silicones when employed as a carrier may be selected from polyalkyl siloxane, polyalkylaryl siloxane or polyether siloxane copolymer (e.g. dimethiconol). Commercially they are available from Dow Corning as, for instance, DC 556 or DC 200 series. Non-volatile silicones when present can range in amount from about 0.1 to about 30%, preferably from about 1 to about 15% by weight.

Esters may also be utilized as a carrier. Illustrative esters are those formed from $C_1$–$C_{20}$ alkanols esterified with $C_8$–$C_{22}$ alkanoic acids. Examples include isopropyl myristate, lauryl myristate, isopropyl palmitate, diisopropyl sebacate and diisopropyl adipate. Most preferred is isopropyl palmitate. Amounts of the ester may range from about 0.5 to about 30%, preferably from 5 to 20%, optimally from about 8 to about 15% by weight.

A number of optional components may also be part of compositions according to the present invention. These include bulking agents, $C_1$–$C_3$ alcohols and powdered fillers.

Bulking or suspending agents when present may be found at levels of from about 1 to about 50%, preferably from about 2 to about 8%.

Clays and colloidal pyrogenic silica are the preferred materials for use as bulking/suspending agents. Colloidal silica is available commercially as Cab-O-Sil®, a submicroscopic particulate pyrogenic silica.

Clay bulking/suspending agents suitable for use in the compositions of the present invention are selected from the group consisting of montmorillonite clays and hydrophobically treated montmorillonite clays. Examples of these clays include the bentonifes, hectorites, and colloidal magnesium aluminum silicates. The latter are complexes of colloidal magnesium aluminum silicate richer in magnesium than aluminum. Commercially they are available as Veegum (R. T. Vanderbilt Co.). Preferred hydrophobically treated montmorillonite clays are available under the trademark of "Bentone". These are prepared by reacting bentonite in a cation exchange system with an amine. Different amines are reacted to obtain a variety of Bentones, which may also differ in proportions of $SiO_2$, MgO and $Al_2O_4$. Specific examples of Bentones within the scope of the present invention are Bentone 38, Bentone 34, Bentone 27, Bentone 14, and Bentone LT, all of which have a particle size of below about 5 microns and are commercially available from Rheox, Inc.

A further benefit of alkyl acetates is the activating function they can perform with respect to clays, especially Bentone® type materials. Normally small amounts of propylene carbonate are formulated to activate the clay but for the present invention the presence of propylene carbonate is unnecessary and may be avoided.

Powdered fillers other than bulking agents may also be incorporated. Particularly preferred is talc, sodium bicarbonate, corn starch, modified starches and mixtures thereof. Most preferred is talc. Amounts of the powdered filler may range from 0.5 to 15%, preferably from about 1 to about 10%, optimally from about 1.5 to about 5% by weight.

Another optional element according to the present invention is that of a $C_1$–$C_3$ alcohol. Most preferred is ethanol, especially SD Alcohol 40. Of course, it is possible also to use methanol or isopropanol. Amounts of the alcohol may range from about 10 to about 70%, preferably from about 12 to about 40%, optimally from 15 to 30% by weight of the composition. In certain products it may be desirable to have an alcohol free formulation or at least limit the amount of alcohol to less than 10%, preferably less than 5% by weight of the composition.

Adjunct minor ingredients can be present including fragrance and anti-clogging agents for keeping the spray nozzle free of solid occlusions.

Although the present invention is specifically advantageous in aerosol formulations, the present invention may also be useful for other antiperspirant forms including roll-on liquids and ultra dry creams.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight of the composition unless otherwise indicated.

EXAMPLES 1–4

A set of aerosol antiperspirant compositions according to the present invention are outlined in Table I.

TABLE I

| | EXAMPLE (WEIGHT %) | | | |
|---|---|---|---|---|
| INGREDIENTS | 1 | 2 | 3 | 4 |
| Cyclomethicone (DC 344 ®) | 25.10 | 15.10 | 25.10 | 15.10 |
| Isopropyl Palmitate | 10.50 | 10.50 | 10.50 | 10.50 |
| Bentone 3BCG ® | 1.50 | 1.50 | 1.50 | 1.50 |
| Methyl Acetate | 10.00 | 20.00 | 10.00 | 20.00 |
| Propylene Carbonate | 0.70 | 0.70 | 0.70 | 0.70 |
| Talc | 3.00 | 3.00 | — | — |
| Corn Starch | — | — | 3.00 | 3.00 |

TABLE I-continued

| INGREDIENTS | EXAMPLE (WEIGHT %) | | | |
|---|---|---|---|---|
| | 1 | 2 | 3 | 4 |
| Aluminum Chlorhydrate | 9.20 | 9.20 | 9.20 | 9.20 |
| A50 Propellant | 40.00 | 40.00 | 40.00 | 40.00 |

EXAMPLES 5–11

A set of aerosol deodorant compositions suitable for the present invention are outlined in Table II.

TABLE II

| INGREDIENTS | EXAMPLE (WEIGHT %) | | | | | | |
|---|---|---|---|---|---|---|---|
| | 2 | 3 | 4 | 5 | 6 | 7 | 8 |
| Cyclomethicone (DC 344 ®) | 10.10 | 10.10 | 10.10 | 15.10 | 15.10 | 15.10 | 20.60 |
| Isopropyl Palmitate | 10.50 | 5.50 | 0.50 | 10.50 | 10.50 | 10.50 | — |
| Triclosan | 1.50 | 1.50 | 0.50 | 3.50 | 3.50 | 1.50 | 1.50 |
| Methyl Acetate | 25.00 | 10.00 | 10.00 | 10.00 | 20.00 | 20.00 | 25.00 |
| Fragrance | 0.70 | 0.70 | 0.70 | 0.70 | 0.70 | 0.70 | 0.70 |
| Talc | 3.00 | 3.00 | 1.00 | 1.00 | 1.00 | 3.00 | 3.00 |
| Sodium Bicarbonate | 9.20 | 9.20 | 7.20 | 19.20 | 9.20 | 9.20 | 9.20 |
| A-31 Propellant | 40.00 | 60.00 | 70.00 | 40.00 | 40.00 | 40.00 | 40.00 |

EXAMPLE 12

A series of aerosol antiperspirant formulations were prepared and charged to respective finplate steel pressurized cans. These formulations were placed on storage for two weeks at 120° F. to evaluate corrosion properties. Table III details the components of these formulations as well as the corrosion results.

TABLE III

| INGREDIENTS | SAMPLE (WEIGHT %) | | | |
|---|---|---|---|---|
| | A | B | C | D |
| Methyl Acetate | 10.0 | 0 | 10.0 | 10.0 |
| Ethanol | 0 | 10.0 | 10.0 | 0 |
| Summit A426 (Aluminum Chlorhydrate) | 9.2 | 9.2 | 9.2 | 0 |
| Reheis Micro Dry (Aluminum Chlorhydrate) | 0 | 0 | 0 | 9.2 |
| Propellant 152A (Hydrogenated Chlorofluorocarbon) | 40.0 | 40.0 | 40.0 | 40.0 |
| Isopropylpalmitate | 10.5 | 10.5 | 10.5 | 10.5 |
| Bentone 38CG ® | 1.5 | 1.5 | 1.5 | 1.5 |
| Fragrance | 0.7 | 0.7 | 0.7 | 0.7 |
| Talc | 3.0 | 3.0 | 3.0 | 3.0 |
| Cyclomethicone | 25.1 | 25.1 | 15.1 | 25.1 |
| Results | No Detinning | Minor Detinning Along Seam of Can | Minor Detinning Along Seam of Can | No Detinning |

Formulations A and D demonstrate that methyl acetate does not impart any detinning or corrosion to the cans. Formulations B and C which include ethanol display the beginning signs of detinning. Methyl acetate is therefore an excellent replacement for ethanol in these formulations.

The foregoing description and examples illustrate selected embodiments of the present invention. In light thereof variations and modifications will be suggested to one skilled in the art, all of which are within the spirit and purview of this invention.

What is claimed is:

1. An underarm compositions comprising:
   (i) from about 0.1 to about 80% by weight of a $C_1$–$C_6$ alkyl acetate;
   (ii) an underarm active selected from the group consisting of astringent salts and anti-microbial agents; and
   (iii) from about 0.1 to about 90% of a pharmaceutically acceptable carrier.

2. The composition according to claim 1 wherein the carrier comprises a propellant.

3. The composition according to claim 1 further comprising from about 0.5 to about 30% by weight of an ester emollient formed from esterification of a $C_1$–$C_{20}$ alcohol with a $C_8$–$C_{22}$ alkanoic acid.

4. The composition according to claim 1 further comprising from about 1 to about 50% by weight of a bulking agent.

5. The composition according to claim 4 wherein the bulking agent is a hydrophobically treated bentonite.

6. The composition according to claim 1 wherein the carrier is cyclomethicone.

7. The composition according to claim 1 wherein the astringent salt is an aluminum salt.

8. The composition according to claim 1 wherein the alkyl acetate is selected from the group consisting of methyl acetate and t-butyl acetate.

9. The composition according to claim 1 wherein propylene carbonate is absent.

* * * * *

UNITED STATES PATENT AND TRADEMARK OFFICE
CERTIFICATE OF CORRECTION

PATENT NO. : 6,096,297
DATED : August 1, 2000
INVENTOR(S) : Jones et al.

It is certified that error appears in the above-identified patent and that said Letters Patent is hereby corrected as shown below:

Title page, item [73],

Change Assignee from "Unilever Home & Personal Care USA,"

to - - Unilever Home & Personal Care USA, Division of Conopco, Inc. - -

Signed and Sealed this

First Day of May, 2001

Attest:

NICHOLAS P. GODICI

*Attesting Officer*   *Acting Director of the United States Patent and Trademark Office*